(12) United States Patent
Shiraki et al.

(10) Patent No.: US 7,282,202 B2
(45) Date of Patent: Oct. 16, 2007

(54) INTERLEUKIN-6 SUPPRESSIVE AGENT

(75) Inventors: Kimiyasu Shiraki, Toyama (JP); Masahiko Kurokawa, Nobeoka (JP); Yoshitaka Tamura, Zama (JP); Koji Yamauchi, Zama (JP); Hiroyuki Wakabayashi, Zama (JP); Kouichirou Shin, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 373 days.

(21) Appl. No.: 10/518,018

(22) PCT Filed: Nov. 25, 2003

(86) PCT No.: PCT/JP03/15009

§ 371 (c)(1),
(2), (4) Date: Dec. 15, 2004

(87) PCT Pub. No.: WO2004/073733

PCT Pub. Date: Sep. 2, 2004

(65) Prior Publication Data

US 2005/0249715 A1    Nov. 10, 2005

(30) Foreign Application Priority Data

Feb. 24, 2003  (JP) ............................. 2003-045509

(51) Int. Cl.
 A61K 38/44  (2006.01)
 A61K 47/00  (2006.01)
(52) U.S. Cl. ...................... 424/94.4; 424/439; 514/714
(58) Field of Classification Search ............... 424/94.4, 424/439; 514/714
 See application file for complete search history.

(56) References Cited

U.S. PATENT DOCUMENTS

| 5,561,109 A * | 10/1996 | Mita et al. ..................... 514/12 |
| 2002/0044989 A1 | 4/2002 | Gaull |
| 2002/0192296 A1 | 12/2002 | Gaull et al. |
| 2003/0012787 A1 * | 1/2003 | Ashkenazi et al. ...... 424/145.1 |
| 2003/0027248 A1 * | 2/2003 | Bejanin et al. ............ 435/69.1 |

FOREIGN PATENT DOCUMENTS

| EP | 0 791 359 A1 | 8/1997 |
| EP | 1 002 542 A1 | 5/2000 |
| JP | 61-83131 | 4/1986 |
| JP | 3-218318 | 9/1991 |
| JP | 05-009124 | 1/1993 |
| JP | 05-092927 | 4/1993 |
| JP | 05-124980 | 5/1993 |
| JP | 6-501453 | 2/1994 |
| JP | 2840795 | 10/1998 |
| JP | 2000-509367 | 7/2000 |
| JP | 2001-226289 | 8/2001 |
| JP | 2002-238554 | 8/2002 |
| WO | WO92/01466 | 2/1992 |

OTHER PUBLICATIONS

Lefkowitz, et al. "Induction of Tumor Necrosis Factor and Cytotoxicity by Macrophages Exposed to Lactoperoxidase and Microperoxidase," *Life Sciences*, vol. 47, No. 8, pp. 703-709, 1990.
Lefkowitz, et al. "Peroxidase-Induced Enhancement of Chemiluminescence by Murine Peritoneal Macrophages," *Life Sciences*, vol. 43, No. 9, pp. 739-745, 1988.
Shin, et al. "Identification of Lactoperoxidase in Mature Human Milk," *Journal of Nutritional Biochemistry*, vol. 11, pp. 94-102, Feb. 2000.
Wong, et al. "Immunomodulatory Activities of Whey Fractions in Efferent Prefemoral Lymph of Sheep," *Journal of Dairy Research*, vol. 63, pp. 257-267, 1996.
Wong, et al. "Influence of Whey and Purified Whey Proteins on Neutrophil Functions in Sheep," *Journal of Dairy Research*, vol. 65, pp. 281-288, 1997.
Wong, et al. "Effects of Purified Bovine Whey Factors on Cellular Immune Functions in Ruminants," *Veterinary Immunology and Immunopathology*, vol. 56, pp. 85-96, 1997.
Haversen, et al. "Human Lactoferrin and Peptides Derived from a Surface-Exposed Helical Region Reduce Experimental *Escherichia coli* Urinary Tract Infection in Mice," *Infection and Immunity*, pp. 5816-5823, Oct. 2000.

* cited by examiner

*Primary Examiner*—Herbert J. Lilling
(74) *Attorney, Agent, or Firm*—Knobbe, Martens, Olson & Bear, LLP

(57) ABSTRACT

An interleukin-6 suppressive agent comprising lactoperoxidase as an active ingredient is used as a pharmaceutical preparation or the like for prevention and/or therapy of a disease caused by production of interleukin-6, such as thrombocytosis, myeloma, Castleman syndrome, rheumatoid arthritis, or influenza-virus infectious disease.

2 Claims, No Drawings

SEQUENCE LISTING

<160> NUMBER OF SEQ ID NOS: 1

<210> SEQ ID NO 1
<211> LENGTH: 612
<212> TYPE: PRT
<213> ORGANISM: Bos taurus

<400> SEQUENCE: 1

```
Asp Thr Thr Leu Thr Asn Val Thr Asp Pro Ser Leu Asp Leu Thr Ala
1               5                   10                  15

Leu Ser Trp Glu Val Gly Cys Gly Ala Pro Val Pro Leu Val Lys Cys
            20                  25                  30

Asp Glu Asn Ser Pro Tyr Arg Thr Ile Thr Gly Asp Cys Asn Asn Arg
        35                  40                  45

Arg Ser Pro Ala Leu Gly Ala Ala Asn Arg Ala Leu Ala Arg Trp Leu
    50                  55                  60

Pro Ala Glu Tyr Glu Asp Gly Leu Ala Leu Pro Phe Gly Trp Thr Gln
65                  70                  75                  80

Arg Lys Thr Arg Asn Gly Phe Arg Val Pro Leu Ala Arg Glu Val Ser
                85                  90                  95

Asn Lys Ile Val Gly Tyr Leu Asp Glu Glu Gly Val Leu Asp Gln Asn
            100                 105                 110

Arg Ser Leu Leu Phe Met Gln Trp Gly Gln Ile Val Asp His Asp Leu
        115                 120                 125

Asp Phe Ala Pro Glu Thr Glu Leu Gly Ser Asn Glu His Ser Lys Thr
    130                 135                 140

Gln Cys Glu Glu Tyr Cys Ile Gln Gly Asp Asn Cys Phe Pro Ile Met
145                 150                 155                 160

Phe Pro Lys Asn Asp Pro Lys Leu Lys Thr Gln Gly Lys Cys Met Pro
                165                 170                 175

Phe Phe Arg Ala Gly Phe Val Cys Pro Thr Pro Pro Tyr Gln Ser Leu
            180                 185                 190

Ala Arg Glu Gln Ile Asn Ala Val Thr Ser Phe Leu Asp Ala Ser Leu
        195                 200                 205

Val Tyr Gly Ser Glu Pro Ser Leu Ala Ser Arg Leu Arg Asn Leu Ser
    210                 215                 220

Ser Pro Leu Gly Leu Met Ala Val Asn Gln Glu Ala Trp Asp His Gly
225                 230                 235                 240

Leu Ala Tyr Leu Pro Phe Asn Asn Lys Lys Pro Ser Pro Cys Glu Phe
                245                 250                 255

Ile Asn Thr Thr Ala Arg Val Pro Cys Phe Leu Ala Gly Asp Phe Arg
            260                 265                 270
```

```
Ala Ser Glu Gln Ile Leu Leu Ala Thr Ala His Thr Leu Leu Leu Arg
        275                 280                 285

Glu His Asn Arg Leu Ala Arg Glu Leu Lys Lys Leu Asn Pro His Trp
        290                 295                 300

Asn Gly Glu Lys Leu Tyr Gln Glu Ala Arg Lys Ile Leu Gly Ala Phe
305                 310                 315                 320

Ile Gln Ile Ile Thr Phe Arg Asp Tyr Leu Pro Ile Val Leu Gly Ser
                325                 330                 335

Glu Met Gln Lys Trp Ile Pro Pro Tyr Gln Gly Tyr Asn Asn Ser Val
        340                 345                 350

Asp Pro Arg Ile Ser Asn Val Phe Thr Phe Ala Phe Arg Phe Gly His
        355                 360                 365

Met Glu Val Pro Ser Thr Val Ser Arg Leu Asp Glu Asn Tyr Gln Pro
        370                 375                 380

Trp Gly Pro Glu Ala Glu Leu Pro Leu His Thr Leu Phe Phe Asn Thr
385                 390                 395                 400

Trp Arg Ile Ile Lys Asp Gly Gly Ile Asp Pro Leu Val Arg Gly Leu
                405                 410                 415

Leu Ala Lys Lys Ser Lys Leu Met Asn Gln Asp Lys Met Val Thr Ser
        420                 425                 430

Glu Leu Arg Asn Lys Leu Phe Gln Pro Thr His Lys Ile His Gly Phe
        435                 440                 445

Asp Leu Ala Ala Ile Asn Leu Gln Arg Cys Arg Asp His Gly Met Pro
450                 455                 460

Gly Tyr Asn Ser Trp Arg Gly Phe Cys Gly Leu Ser Gln Pro Lys Thr
465                 470                 475                 480

Leu Lys Gly Leu Gln Thr Val Leu Lys Asn Lys Ile Leu Ala Lys Lys
                485                 490                 495

Leu Met Asp Leu Tyr Lys Thr Pro Asp Asn Ile Asp Ile Trp Ile Gly
                500                 505                 510

Gly Asn Ala Glu Pro Met Val Glu Arg Gly Arg Val Gly Pro Leu Leu
        515                 520                 525

Ala Cys Leu Leu Gly Arg Gln Phe Gln Gln Ile Arg Asp Gly Asp Arg
        530                 535                 540

Phe Trp Trp Glu Asn Pro Gly Val Phe Thr Glu Lys Gln Arg Asp Ser
545                 550                 555                 560

Leu Gln Lys Val Ser Phe Ser Arg Leu Ile Cys Asp Asn Thr His Ile
                565                 570                 575

Thr Lys Val Pro Leu His Ala Phe Gln Ala Asn Asn Tyr Pro His Asp
                580                 585                 590

Phe Val Asp Cys Ser Thr Val Asp Lys Leu Asp Leu Ser Pro Trp Ala
        595                 600                 605

Ser Arg Glu Asn
        610
```

INTERLEUKIN-6 SUPPRESSIVE AGENT

This application is the U.S. National Phase under 35 U.S.C. § 371 of International Application PCT/JP2003/015009, filed Nov. 25, 2003, which was published in a language other than English, which claims priority of JP 2003-45509, filed on Feb. 24, 2003.

TECHNICAL FIELD

The present invention relates to an interleukin-6 suppressive agent comprising lactoperoxidase as an active ingredient. More specifically, the present invention relates to an interleukin-6 suppressive agent that has effects in the prevention and/or therapy of disease caused by an abnormal production of interleukin-6 and to an interleukin-6 suppressive agent that can be applied in food and drink, feed, or the like.

BACKGROUND ART

An inflammatory reaction is a kind of biological defense reaction to tissue damage to be caused by various kinds of invasion and is featured by associated symptoms such as: flare, swelling, pyrexia, and pain. Bioactive substances involved in the inflammatory reaction include so-called inflammatory mediators such as histamine, serotonin, and prostaglandin and so-called inflammatory cytokines such as interleukin-1, interleukin-6, interleukin-8, and tumor necrosis factors (TNFs), which are produced by various kinds of cells such as leukocytes (e.g., Shogo Karino, Nobuyuki Miyasaka, and Nagahiro Minato Ed., "Clinical Immunology", Asakura-Shoten, 1997, p. 73-77).

Interleukin-6 is a polypeptide cytokine consisting of 184 amino acids with a molecular weight of 21 to 28 kDa. Interleukin-6 can be produced from a wide variety of cells such as vascular endothelial cells, T-lymphocytes, B-lymphocytes, monocytes, and macrophages by various kinds of stimulative substances such as lipopolysaccharide, interleukin-1, and TNFs, which can be found in the site of inflammation. As the biological actions of interleukin-6, important actions have been reported, including the acceleration of the synthesis of acute-phase inflammatory protein, induction of the antibody production by B-cells, and the activation of T-lymphocytes. On the other hand, it has been suggested that the abnormality in production of interleukin-6 may deeply relate to various kinds of immunopathy, inflammatory diseases, and lymphoid tumors (e.g., Masahiro Matsumura, Ed., "Dictionary of Molecular Cell Biology", Tokyo Kagaku Dojin Co., Ltd., 1997, p. 90).

On the other hand, interleukin-6 antibody and interleukin-6 receptor antibody, which inhibit the action of inerleukin-6, have been expected to show effectiveness on various kinds of inflammatory diseases such as autoimmune diseases including rheumatoid arthritis and the like, psoriasis, atrial myxoma, mesangial proliferative nephritis, Castleman syndrome, AIDS, and multiple myeloma (e.g., "Clinical Immunology", Asakukra-Shoten, 1997, P. 73-77). A therapeutic agent for a disease caused by the production of an interleukin-6 using an antibody against interleukin-6 receptor as an active ingredient (e.g., JP 8-169846 A) and a composition for suppressing interleukin-6 produced by cultured mammalian cells (JP 8-99996 A) have been already disclosed. In addition, it is revealed that, when the anti-inflammatory agent, indomethacin is administered to rats with carrageenan-induced pleurisy, pleuritic inflammation is restrained significantly and interleukin-6 in a peritoneal exudation is inhibited (e.g., "Yakugaku Zasshi", vol. 120, 2000, p. 455-462).

Regarding the involvement of proteins in milk to interleukin-6, there has been to date disclosed each of the suppressive action of lactoferrin on the urinary level of interleukin-6 in an *Escherichia coli* urinary tract infection mouse (e.g., "Infection and Immunity", U.S.A., vol. 68, 2000, p. 5816-5823) and a composition for regulating the ability to produce interleukin containing fermented milk or a processed product thereof as an active ingredient (e.g., JP 5-9124 A).

Lactoperoxidase, one of the milk proteins, is an oxidoreductase not only contained in mammalian milk but also contained in secretions such as saliva, tears, and respiratory mucus (e.g., "American Journal of Respiratory and Critical Care Medicine", U.S.A., vol. 166, 2002, p. S57-S61), which are industrially purified in large volumes from milk (e.g., JP 5-41981 A).

Various biological functions of lactoperoxidase have been reported, such as antibacterial activity, antiviral activity, antioxidative activity, anticancer activity, and immunoregulating activity (e.g., "Journal of Nutritional Biochemistry", U.S.A., vol. 11, 2000, p. 94-102; "Life Sciences", U.S.A., vol. 43, 1988, p. 739-745; "Life Sciences", U.S.A., vol. 47, 1990, p. 703-709; "Journal of Dairy Research", U.K., vol. 63, 1996, p. 257-267; "Journal of Dairy Research", U.K., vol. 64, 1997, p. 281-288; "Veterinary Immunology and Immunopathology", Holland, vol. 56, 1997, p. 85-96). There are disclosed technologies with respect to the use of lactoperoxidase, peroxide donor, and thiocyanate for the production of therapeutic pharmaceuticals for *Helicobacter pylori* infection (e.g., JP 2000-509367 A), a preventive and therapeutic agent for the infection of pathogenic bacteria to be added in the mixed feed of farmed aquatic animals (e.g., JP 3103615 B), an age resistor (JP 3103167 B), and a liver-function improving agent (e.g., JP 2001-226289 A), the preventive and therapeutic application of peroxidase (e.g., JP 6-501453 A), and a therapeutic agent for corneal disorder (e.g., JP 2840795 B). Furthermore, the applicant of the present invention has already disclosed a urease-inactivating composition in which peroxidase, thiocyanic acid, and hydrogen peroxide are provided as active ingredients (disclosed in JP 2002-238554 A). However, there has been to date no reports on existing technology at all about the effect of lactoperoxidase on the production of one of inflammatory cytokines, ineterleukin-6.

DISCLOSURE OF THE INVENTION

In consideration of the background art, the inventors of the present invention have found for the first time that lactoperoxidase, which is a milk protein, has a suppressive action on the production of interleukin-6 as a result of extensive studies mainly on food materials such as proteins with respect to an interleukin-6 suppressive agent with safety and few side effects, which can be administered on a daily basis for a long time. As a result, it is revealed that the symptoms of various kinds of infectious diseases and inflammatory diseases caused by the production of interleukin-6 can be relieved by the use of lactoperoxidase.

In order to solve the above-mentioned problems, the present invention provides an interleukin-6 suppressive agent comprising lactoperoxidase as an active ingredient.

According to a preferred aspect of the interleukin-6 suppressive agent, the interleukin-6 suppressive agent is a pharmaceutical preparation for preventing and/or treating a disease caused by the production of interleukin-6.

The present invention further provides a food and drink composition or a feed composition, which is prepared by adding the interleukin-6 suppressive agent.

The present invention further provides a use of lactoperoxidase for manufacture of a pharmaceutical preparation for preventing and/or treating a disease caused by production of interleukin-6.

The present invention further provides a method of preventing or treating a disease by administering an interleukin-6 suppressive agent comprising lactoperoxidase as an effective ingredient to an object person who requires prevention or therapy of a disease caused by production of interleukin-6.

In the present invention, the disease caused by the production of interleukin-6 includes thrombocytosis, myeloma, Castleman syndrome, cardiac myxoma, glomerulonephritis, rheumatoid arthritis, sepsis, and influenza-virus infectious disease.

The present invention provides a pharmaceutical preparation effective to prevention and/or therapy of a disease caused by the production of interleukin-6, which excels in safety, enables mass-production at low costs, and has an effective suppressive action against the production of interleukin-6.

Among the matters described in the background art, the technology highly related to the present invention is different from the present invention in following points:

(1) The effective ingredient of the therapeutic agent for disease caused by the production of interleukin-6 as disclosed in JP 8-169846 A is an antibody against an interleukin-6 receptor, which is different from lactoperoxidase provided as the active ingredient of the present invention.

(2) The composition having the interleukin-6 suppressing activity as disclosed in JP 8-99996 A has a molecular weight of 10 kDa or 44 kDa, which is different from the molecular weight of the active ingredient, lactoperoxidase, that is, 80 kDa, of the present invention, and also no description about lactoperoxidase cannot be found in the publication at all.

(3) "Infection and Immunity", U.S.A., vol. 68, 2000, p. 5816-5823, describes the suppressive action of the urinary level of interleukin-6 of an *E. coli* urinary tract infection mouse with lactoferrin. However, it is different from lactoperoxidase provided as the active ingredient of the present invention; the publication has no description at all about lactoperoxidase.

(4) In JP 5-9124 A, there is described a composition for suppressing the ability to produce interleukin-6, which contains fermented milk or a processed product thereof as an active ingredient and there is exemplified animal milk as a raw material of the fermented milk provided as the active ingredient, but there is no description at all about lactoperoxidase provided as the active ingredient of the present invention. It is considered that, even if the fermented milk has a suppressive effect on the ability to produce interleukin-6, the effect of the fermented milk itself would hardly lead the interluekin-6 suppressive effect of lactoperoxidase.

BEST MODE FOR CARRYING OUT THE INVENTION

Hereinafter, preferred embodiments of the present invention will be described in detail. However, the present invention is not limited to the preferred embodiments described below, so that it can be modified within the scope of the present invention. In addition, unless otherwise specified, percentage is represented by mass in this specification.

Lactoperoxidase to be used in the present invention can be obtained from milk or the like of a human, a cow, a horse, a sheep, or a goat. For example, like a method as disclosed in JP 5-41981 A (title of the invention: viable cell-containing liquid composition), preferable is an industrial production from whey or skimmed milk of unheated milk or the like according to the conventional method (e.g., ion-exchange chromatography). Furthermore, it is also possible to use commercially available lactoperoxidase originated from natural products (e.g., produced by Biopole), or recombinant lactoperoxidase (e.g., recombinant lactoperoxidase expressed and purified by the method of Shin et al., "Biochemical and Biophysical Research Communications", vol. 271, 2000, p. 831-836, or commercially available recombinant lactoperoxidase) (e.g., produced by Biopole).

Examples of lactoperoxidase, which can be used in the present invention, include engineered products of lactoperoxidase as described above. Specifically, the engineered product can be exemplified by a protein including a protein having of a sequence with substitutions, deletions, or additions of one or several amino acids in the amino acid sequence of EMBL-Accession No.: M58150 or SEQ ID NO: 1, EMBL-Accession No.: AY324876, EMBL-Accession No.: AF027970, or the like. The term "several" means 2 to 50, preferably 2 to 20, particularly preferably 2 to 10. In addition, the engineered product can be exemplified by a protein having a sequence which has homology of 70% or more, preferably 80% or more, more preferably 90% or more, particularly preferably 95% or more to the amino acid sequence of EMBL-Accession No.: M58150 or SEQ ID NO: 1, EMBL-Accession No.: AY324876, EMBL-Accession No.: AF027970, or the like. Preferably, those engineered products of lactoperoxidase may be modified so as to retain a suppressive action on the production of interleukin-6 and to lower the antigenicity against a human as far as possible. The lactoperoxidase-engineered product can be obtained by allowing a gene encoding wild-type lactoperoxidase to be mutated by a PCR method or the like to express the mutant gene in a well-known expression system, and determining the suppressive action of the resulting protein on the production of interleukin-6. Furthermore, it can also be obtained such that a microorganism or the like in which a wild-type lactoperoxidase-encoding gene is introduced is subjected to mutagenic treatment with UV irradiation or the like and then a lactoperoxidase engineered product is purified from the resulting microorganism to determine the suppressive action on the production of interleukin-6. In this regard, the "engineered products" used herein are not necessarily prepared by engineering the wild type, so that they may be mutants as naturally occurring ones. In addition, when lactoperoxidase is added to food and drink and feed when in use, it is preferable to use the wild-type lactoperoxidase in which any amino acid is as less subjected as possible to substitution, deletion, addition, or the like.

Lactoperoxidase has a suppressive action on the production of interleukin-6, so that it can be used as an active ingredient for an interleukin-6 suppressive agent (hereinafter, also referred to as "suppressive agent of the present invention"). Here, the "active ingredient" means an ingredient that shows a suppressive effect on the production of interleukin-6. Thus, the suppressive agent of the present invention does not have to contain lactoperoxidase as a main ingredient. Besides, other than lactoperoxidase, the suppressive agent of the present invention may contain an ingredient having a suppressive action on the production of interleukin- 6. For example, other than lactoperoxidase, the inhibitor of the present invention may contain an ingredient having a suppressive action on the production of interleukin-6, other useful proteins in milk such as casein, α-lactalbumin, and β-lactoglobulin.

The interleukin-6 suppressive agent of the present invention may contain, in addition to lactoperoxidase, a partial peptide of lactoperoxidase or a hydrolysate mixture (peptides mixture) of lactoperoxidase. In addition, it may contain partial peptide(s) of lactoperoxidase having a suppressive action on the production of interleukin-6 or a hydrolysate mixture (a peptide mixture) of lactoperoxidase as an active ingredient.

The interleukin-6 suppressive agent of the present invention has a suppressive action on the production of interleukin-6 that is a kind of inflammatory cytokines produced in the living body, and thus can be used as pharmaceutical preparations such as those having soothing effects on the symptoms of various kinds of infectious and inflammatory diseases, such as thrombocytosis, myeloma, Castleman syndrome, cardiac myxoma, glomerulonephritis, rheumatoid arthritis, sepsis, and influenza-virus infectious disease, through the suppression of the interleukin-6 production. However, the application of the suppressive agent of the present invention is not limited to prevention and/or therapy of the disease caused by an abnormal production of interleukin-6.

The active ingredient of the interleukin-6 suppressive agent of the present invention is included in food materials such as milk protein, so that the interleukin-6 suppressive agent of the present invention is high in safety to human beings and has such characteristic that its effect is exerted on prevention and/or therapy to the disease caused by the production of interleukin-6 by daily oral intake thereof as a composition contained in food and drink.

The forms of the interleukin-6 suppressive agent of the present invention include, but are not particularly limited to, pharmaceutical compositions, food and drink compositions, and feed compositions. In other words, an embodiment of the suppressive agent of the present invention is a pharmaceutical preparation for the prevention and/or therapy of the disease caused by the production of interleukin-6, which contains lactoperoxidase as an active ingredient. In addition, another embodiment of the present invention is the use of lactoperoxidase for manufacture of a pharmaceutical preparation for the prevention and/or therapy of the disease caused by the production of interleukin-6. In a preferred embodiment, the suppressive agent of the present invention is administered to an object person who requires the prevention or therapy of the disease caused by the production of interleukin-6 to prevent or medicate the disease. Furthermore, in another embodiment, the suppressive agent of the present invention is added to a raw material of a food and drink composition or a raw material of a feed composition to make up the food and drink composition or the feed composition.

The examples of disease caused by the production of interleukin-6 include various kinds of infectious diseases, inflammatory diseases, and the like, for example, thrombocytosis, myeloma, Castleman syndrome, cardiac myxoma, glomerulonephritis, rheumatoid arthritis, sepsis, and influenza-virus infectious disease.

The suppressive agent of the present invention may be lactoperoxidase itself or may contain an ingredient other than lactoperoxidase. The ingredient other than lactoperoxidase can be suitably selected depending on the dosage form. For example, various kinds of food and drink may be prepared by mixing with lactoperoxidase powder, an aqueous lactoperoxidase solution (e.g., syrup), or the like as the interleukin-6-suppressive agent of the present invention.

The pharmaceutical composition can be produced by pharmaceutically formulating lactoperoxidase using pharmaceutically acceptable excipient and any other additives, and the pharmaceutically-formulated lactoperoxidase can be used as preventative and/or therapeutic agents against a disease caused by the production of interleukin-6. In the case of pharmaceutical formulation, the content of lactoperoxidase in a pharmaceutical preparation is generally 0.001 to 20% by mass, preferably 0.1 to 15% by mass. For pharmaceutical formulation, additives such as excipients, binders, disintegrating agents, lubricants, stabilizers, flavoring agents, diluents, and injection solvent can be used.

The excipients include: saccharide derivatives such as lactose, saccharose, glucose, mannitol, and sorbit; starch derivatives such as corn starch, potato starch, α-starch, dextrin, and carboxymethyl starch; cellulose derivatives such as crystal cellulose, hydroxypropyl cellulose, hydroxypropyl methylcellulose, carboxymethyl cellulose, and calcium carboxymethyl cellulose; gum Arabic; dextran; pullulan; silicate derivatives such as light silicic anhydride, synthetic silica aluminum, and bisilicate magnesium aluminate; phosphate derivatives such as calcium phosphate; carbonate derivatives such as calcium carbonate; and sulfate derivatives such as calcium sulfate. Binders include, in addition to the excipients described above: gelatin; polyvinyl pyrrolidone; and magrogol, for example. Disintegrating agents include, in addition to the excipients described above, chemically-modified starch or cellulose derivatives such as croscarmellose sodium, carboxymethyl starch sodium, and cross-linked polyvinyl pyrrolidone, for example. Lubricants include: talc; stearic acid; metal stearates such as calcium stearate and magnesium stearate; colloidal silica; waxes such as Veegum and spermaceti; boric acid; glycol; carboxylic acids such as fumaric acid and adipic acid; sodium carboxylate such as sodium benzoate; sulfate salts such as sodium sulfate; leucine; lauryl sulfates such as sodium lauryl sulfate and magnesium lauryl sulfate; silic acids such as silicic anhydride and silicic hydrate; and starch derivatives, for example. Stabilizers include: p-hydroxybenzoate esters such as methylparaben and propylparaben; alcohols such as chlorobutanol, benzyl alcohol, and phenylethyl alcohol; benzalkonium chloride; acetic anhydride; and sorbic acid, for example. Flavoring agents include sweeteners, acidifiers, and perfume, for example. Injection solvents include, for example, water, ethanol, and glycerin.

The routes of administration for the pharmaceutical composition include oral administration and non-oral administration such as enteral administration. Dosage forms for the administration of the pharmaceutical composition include spray, capsules, tablets, granules, syrup, emulsion, suppository, injection, ointment, and tapes, for example.

In addition, the interleukin-6 suppressive agent of the present invention can be also administered by blending it in food and drink, feed, and the like. The dosage and the number of doses vary depending on intended effects, administration method, duration of treatment, age, body weight, and the like. The dosage can be suitably selected from 10 mg to 10 g per day for an adult in general, and the number of doses can be suitably selected from once to several times per day. In addition, a dosing period is preferably 7 days or more.

The forms of the food and drink compositions mixed with the lactoperoxidase of the present invention, include: soft drinks in which lactoperoxidase powder, an aqueous lactoperoxidase solution (e.g., syrup), or the like is mixed as an interleukin-6 suppressive agent of the present invention, milk beverage or concentrated stock solutions of these beverages, and conditioning powder thereof; dairy products such as processed milk and fermented milk; enteral nourishing foods; and functional foods.

As a form of the food and drink composition, a tablet-shaped supplement can be encompassed. It eliminates the need to control the food intake and calorie per day in consideration of the intake of other foods, while the intake of the active ingredient can be precisely grasped.

Furthermore, the food and drink composition or feed composition of the present invention can be provided as a food and drink composition or feed composition having an indication of its efficiency for the prevention or therapy of a disease described below. In other words, it is possible to indicate that the composition is provided for the prevention or therapy of a disease caused by the production of interleukin-6 such as thrombocytosis, myeloma, Castleman syndrome, cardiac myxoma, glomerulonephritis, rheumatoid arthritis, sepsis, and influenza-virus infectious disease.

The term "indication" means an action to inform a demander of the efficiency, for example, an action to provide a product of the food and drink composition or feed composition of the present invention, or a package and advertisement of the product, or the like with the efficiency, and an action to transfer, deliver, or display the product provided with the efficiency. In particular, a preferable embodiment thereof is indication as food for specified health uses (see the enforcement regulations of Health Promotion Law (Apr. 30, 2003, Item 86 of the Health, the Japanese Ministry of Health, Labor and Welfare) Section 12 (1), Item 5).

In the present invention, for evaluating a suppressive action on the production of interleukin-6 by lactoperoxidase, on the basis of a report that describes the induction of interleukin-6 production with the infection of influenza virus in human beings and mammals ("Journal of Medical Virology", U.S.A., vol. 64, 2001, p. 262-269; and "Circulation", U.S.A., vol. 103, 2001, p. 2283-2288), the inventors of the present invention have studied the effect of lactoperoxidase against the induction of interleukin-6 production in a model mouse infected with influenza virus (the suppressive action on interleukin-6 production, suppressive action on an increase in the number of inflammatory cells, and suppressive action on lung consolidation (severity of pneumonia symptom)). As regards the details thereof, a method of test examples described herein is used.

Hereinafter, the action of the interleukin-6 suppressive agent will be described in detail with reference to the test examples.

TEST EXAMPLE 1

This examination was conducted to investigate the effects of lactoperoxidase on interleukin-6 produced by inflammation with virus infection, the number of inflammatory cells, and the severity of lung consolidation.

(1) Sample Preparation

A test sample was prepared by dissolving lactoperoxidase (produced by Biopole) in purified water so as to have a concentration of 12.5% by mass. As a control sample, purified water was used.

(2) Test Method (a) Administration of Sample

12 Seven-week-old female BALB/C mice (purchased from Nippon SLC) in total were placed in a cage equipped with a coprophagy preventing net and then fed for an acclimatization period of one week with standard pellets (produced by Clea Japan) and drinking water. Subsequently, the mice were divided into two groups of 6 animals each. Then, a control group was obtained by orally administering 0.5 ml of the control sample to one group through a feeding tube. A test group was obtained by orally administering 0.5 ml of the test sample to the other group. These oral administrations were started a day before virus infection and were then successively conducted once a day for 7 days from the start of the administration. At the date of virus infection (second day from the start of sample administration), all of the mice were intranasally inoculated with 10 µl of a phosphate buffer containing 660 PFU (PFU: Plaque-Forming Unit) of an influenza virus A/PR/8/34 (H1N1) strain under anesthesia. The mice were dissected after 6 days from the infection (the final day of sample administration) and various measuring samples shown below were collected.

(b) Collection of Measuring Sample

Serum samples were collected from the mice after the sample administration by collecting blood from the orbital vein thereof under anesthesia, respectively. In addition, a needle was inserted into the trachea after dissection and then 1 ml of a serum-free eagle MEM culture medium (produced by Nissui Pharmaceutical) was injected using an injector, followed by collecting the liquid into the same syringe. The similar injection and collection were repeated two more times, so that bronchoalveolar lavage fluids of the three times in total were collected. The collected bronchoalveolar lavage fluid was centrifuged at 1000 rpm and separated into a cellular fraction and a supernatant. The cellular fraction was provided as an inflammatory cell sample and the supernatant was provided as a bronchoalveolar lavage fluid supernatant sample. Furthermore, lungs were collected from the dissected mice and provided as lung consolidation samples.

(c) Measurement of Interleukin-6 Concentration

The concentrations of interleukin-6 in the serum sample and the bronchoalveolar lavage fluid sample were measured using an ELISA method and the measured values of 6 animals in one group were averaged.

(d) Measurement of Number of Inflammatory Cells

For the inflammatory cell samples, the number of inflammatory cells was measured using a cell-number measuring device (manufactured by Nihon Koden Corporation) and the measured values of 6 animals in one group were averaged.

(e) Scoring the Severity of Lung Consolidation

The severity of consolidation as an inflammatory index of virus infection was scored from 0 (no consolidation) to 10 (sever consolidation) according to the method of Ginsberg et al., "Journal of Experimental Medicine", U.S.A., vol. 95, 1952, p. 135-145) and the measured values of 6 animals in one group were averaged.

(3) Test Results

The results of this test are shown in Tables 1, 2, and 3, respectively. Table 1 shows the measurement results of the respective concentrations of interleukin-6 in the serum sample and the bronchoalveolar lavage fluid supernatant sample. Table 2 shows the results of measuring the number of inflammatory cells in the bronchoalveolar lavage fluid. Table 3 shows the lung consolidation scores.

As a result, as is evident from Table 1, it was found that the concentrations of interleukin-6 in the serum sample and the bronchoalveolar lavage fluid supernatant sample were significantly decreased by the administration of lactoperoxidase to virus-infected mice, respectively.

In addition, as is evident from Table 2, an effect of lactoperoxidase that suppressed the exudation of the inflammatory cells was also confirmed as the number of inflammatory cells in the bronchoalveolar lavage fluid was decreased by the administration of lactoperoxidase.

Furthermore, as is evident from Table 3, the suppressive effect of lactoperoxidase on the lung inflammation was also confirmed such that the lung consolidation score was 5.0 in the control group, but in the test group administered with lactoperoxidase it was decreased to 1.8.

Therefore, lactoperoxidase had a suppressive effect on the production of interleukin-6 in vivo in an effective manner. Thus, depending on such an effect, it was revealed that the suppressive action on the exudation of inflammatory cells and the effect of improving inflammatory symptoms of the lungs were brought out.

Furthermore, when the content of virus in the supernatant of the bronchoalveolar lavage fluid was measured by a plaque method using MDCK cells ("Journal of General Virology), U.K., vol. 71, 1990, p. 2149-2155), there was no difference in content of virus between the control group and the test group with respect. From this, it was confirmed that lactoperoxidase had no anti-virus effect directly on influenza virus in the living body.

TABLE 1

| | Interleukin-6 concentration (pg/ml) | |
|---|---|---|
| | Serum sample | Bronchoalveolar lavage fluid supernatant sample |
| Test group | 59 | 998 |
| Control group | 198 | 4358 |

TABLE 2

| | Number of inflammatory cells ($\times 10^5$ cells/ml) |
|---|---|
| Test group | 4.6 |
| Control group | 9.6 |

TABLE 3

| | Lung consolidation score |
|---|---|
| Test group | 1.8 |
| Control group | 5.0 |

EXAMPLES

Hereinafter, the present invention will be described in more detail with reference to examples. However, the present invention is not limited to the following examples.

Example 1

A parenteral injection having the following composition with a suppressive effect on the production of interlukin-6 was manufactured by the conventional method.

| | |
|---|---|
| Lactoperoxidase (produced by Biopole): | 2.0(%) |
| Actinomycin D (produced by Sigma): | 0.005 |
| Sodium chloride: (produced by Wako Pure Chemical Industry) | 0.9 |
| Mannitol (produced by Kanto Chemical): | 1.0 |
| Distilled water for injection: (Otsuka Pharmaceutical) | 96.095 |

Example 2

7,000 capsules having a suppressive effect on the production of interleukin-6 were obtained by sieving 600 g of lactose (produced by Meggle GmbH), 400 g of corn starch (produced by Nisshin Seifun Group Inc.), 400 g of crystalline cellulose (produced by Wako Pure Chemical Industry), and 600 g of lactoperoxidase through a 50-mesh sieve (manufactured by Yamato Scientific), putting into a polyethylene bag with a thickness of 0.5 mm, mixing by inversion, and filling the powder into capsules (manufactured by Nippon Elanco, No. 1 gelatin capsules, Op. Yellow No. 6 Body, and an empty weight of 75 mg) in an amount of 275 mg by using an automatic capsule filling machine (manufactured by Cecere Pedini; press type).

Example 3

A water phase was prepared in a tank by dissolving 10.8 kg of an enzymatically-hydrolyzed whey protein (produced by Morinaga Milk Industry), 36 kg of dextrin (manufactured by Showa Sangyo), and small amounts of water-soluble vitamins and minerals in 200 kg of water. Concurrently, an oil phase was prepared by mixing and dissolving 3 kg of soy bean salad oil (produced by Taiyo Yushi), 8.5 kg of palm oil (produced by Taiyo Yushi), 2.5 kg of safflower oil (produced by Taiyo Yushi), 0.2 kg of lecithin (produced by Ajinomoto), 0.2 kg of fatty acid monoglyceride (produced by Kao Corporation), and a small amount of fat-soluble vitamins. The oil phase was added to the water phase in the tank and mixed by stirring, followed by heating up to 70° C. and homogenizing at a pressure of 14.7 MPa with a homogenizer. Subsequently, after 10-minute sterilization at 90° C., approximately 59 kg of intermediate product powder was prepared by condensation and spray drying. In 50 kg of the intermediate product powder, 6.8 kg of saccharose (produced by Hokuren), 167 g of amino-acids mixture powder (produced by Ajinomoto), and 60 g of lactoperoxidase (produced by Biopole) were added, followed by uniformly mixing them to produce 56 kg of enteral nourishing food powder containing lactoperoxidase as the interleukin-6 suppressive agent.

Example 4

1,800 (approximately 900 g) tablets containing lactoperoxidase as an interleukin-6 suppressive agent was manufactured such that 150 g of lactoperoxidase (produced by Biopole), 100 g of Lactulose powder (produced by Morinaga Milk Industry), 635 g of malto-dextrin (produced by Matsutani Chemical Industry), 85 g of skim milk (produced by Morinaga Milk Industry), 1 g of stevia sweetener (produced by San-Ei Gen F.F.I.), 5 g of yogurt flavor (produced by San-Ei Gen F.F.I.), and 24 g of a glycerin fatty acid ester pharmaceutical preparation (produced by Riken Vitamin) were added and uniformly mixed, and then the mixed powder was subjected to continuous tablet making using a tableting machine (manufactured by Hata Tekkojo) under conditions of 0.5 g per tablet, a tableting speed of 12 tablets/minute, and a pressure of 9.8 KPa.

INDUSTRIAL APPLICABILITY

As described above in detail, the present invention relates to the interleukin-6 suppressive agent containing lactoperoxidase as an active ingredient and to the use thereof. The present invention exerts the following effects:

(1) It is possible to suppress the production of interleukin-6, effectively.

(2) There is an effect in the prevention or therapy of a disease caused by the production of interleukin-6.

(3) A mass production from raw materials such as milk can be attained at low costs.

(4) Daily intake can be allowed because of high-safety to humans.

(5) A food and drink composition or feed composition having an indication representing that it is provided for the prevention or therapy of a disease caused by the production of interleukin-6 can be provided.

What is claimed is:

1. A method of treating a disease, comprising administering an interleukin-6 suppressive agent comprising lactoperoxidase as an effective ingredient to an object person who requires therapy of a disease caused by production of interleukin-6.

2. The method according to claim 1, wherein the disease caused by the production of interleukin-6 is thrombocytosis, myeloma, Castleman syndrome, cardiac myxoma, glomerulonephritis, rheumatoid arthritis, sepsis, or influenza-virus infectious disease.

* * * * *